United States Patent [19]
Hounsfield et al.

[11] 3,999,073
[45] Dec. 21, 1976

[54] APPARATUS FOR EXAMINING A BODY BY MEANS OF PENETRATING RADIATION

[75] Inventors: Godfrey Newbold Hounsfield, Newark; Anthony Michael Williams, Iver, both of England

[73] Assignee: EMI Limited, Hayes, England

[22] Filed: Dec. 12, 1974

[21] Appl. No.: 532,188

[30] Foreign Application Priority Data
Dec. 13, 1973 United Kingdom ............ 57715/73

[52] U.S. Cl. .......................... 250/445 T; 250/360; 250/510
[51] Int. Cl.² ...................................... G01N 23/02
[58] Field of Search ........ 250/359, 360, 510, 445 T

[56] References Cited
UNITED STATES PATENTS

| | | | |
|---|---|---|---|
| 3,715,587 | 2/1973 | Burkhalter et al. | 250/510 X |
| 3,755,672 | 8/1973 | Edholm et al. | 250/510 X |
| 3,778,614 | 12/1973 | Hounsfield | 250/366 |
| 3,867,634 | 2/1975 | Hounsfield | 250/510 |

*Primary Examiner*—Archie R. Borchelt
*Attorney, Agent, or Firm*—Fleit & Jacobson

[57] ABSTRACT

Apparatus is described for performing a computerized axial tomographic examination of a body. The apparatus contains a source of x-radiation and detector devices mounted to face one another across an opening for the body, the source being arranged to project said radiation in a plane towards the detector devices. The source and detector devices are rotated about an axis passing through said opening and means are disclosed for locating the body in said opening and for adapting the apparatus to accommodate a body which is not centrally located in said opening.

6 Claims, 12 Drawing Figures

APPARATUS FOR EXAMINING A BODY BY MEANS OF PENETRATING RADIATION

This invention relates to apparatus for examining a body by means of penetrating radiation, such as X-radiation, and it relates in particular to such apparatus for examining human patients.

In U.S. Pat. No. 3,778,614, which is equivalent to British Pat. specification No. 1,283,915, apparatus is described for examining thin sectional slices of the human body by means of penetrating radiation, and for reconstructing an image of the variable transmission or absorportion of the elements of the section of the body, with respect to said radiation. One form of apparatus according to this British patent secification is now in use for examining the human head. In this apparatus, accurate positioning of the head relative to the source of radiation, and to the means for detecting the radition after passage through the head, is necessary to ensure accurate image reconstruction. The required accuracy of positioning is achieved by supporting the head in a pouched flexible member forming one wall of water reservoir. When the reservoir is filled with water, the flexible member serves to hold the head firmly but gently. The source of radiation and the detecting means are scanned relative to the head supported in the pouched flexible member, the scanning movements including a step by step rotation of the source of radiation and detecting means. The water reservoir, apart from its flexible wall, participates in this rotation, and the reservoir in addition to its function of supporting the head, acts as an attenuator serving in all angular positions to compensate substantially for variations in the path length for the radiation across the width of the head.

The expedient used in the case of a head machine however gives rise to difficulties if other parts of the body have to be examined. One reason for such difficulties is that it is impracticable to use a flexible pouched member for support if for example, the torso or other intermediate parts of the body have to be examined. Moveover provision has to be made to accommodate a much greater variety of sizes than in the case of the head. Additionally if the body is not centered exactly on the axis of the scan then individual beams of radiation will intersect different thicknesses of the body during the course of the scan.

It is an object of this invention to provide apparatus for examining a body by means of radiation such as X- or γ-radiation in which a radiation source is caused to generate a fan-shaped beam of radiation which is directed through the body from many angular positions relative thereto, and wherein difficulties associated with the different paths relative to the body traversed by radiation in different parts of the fan-shaped beams are reduced or eliminated.

It is another object of this invention to provide apparatus which can accommodate eccentric mounting of a patient's body therein.

In order that the invention may be clearly understood and readily carried into effect, the same will now be described with reference to the accompanying drawings in which.

Figure 1:
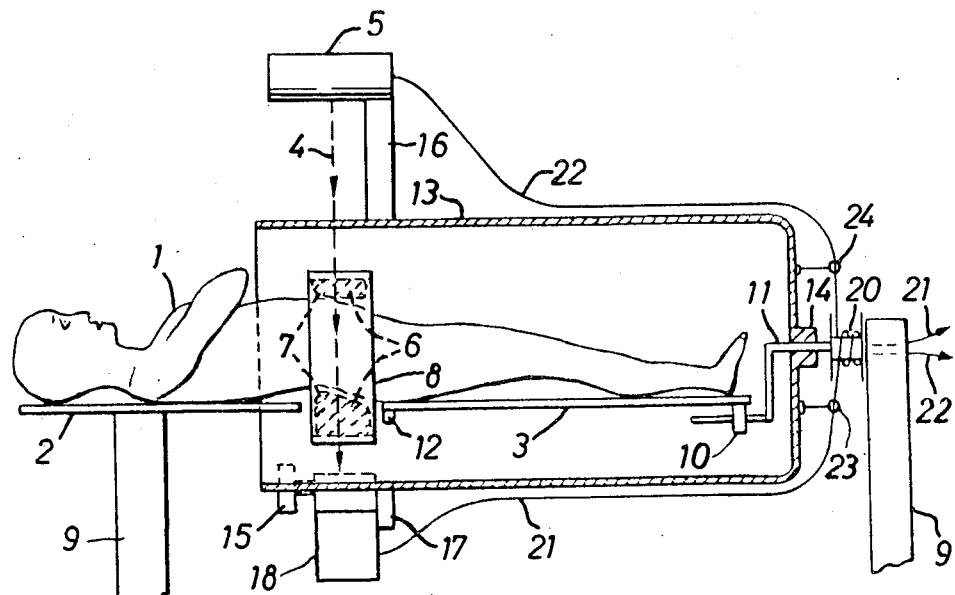
FIG. 1 shows the general layout in side elevation of an apparatus in accordance with one example of the invention.
Figure 2:
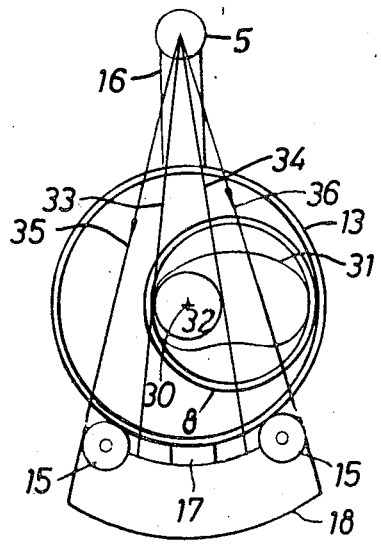
FIG. 2 illustrates the same apparatus in end elevation view.
Figure 3:
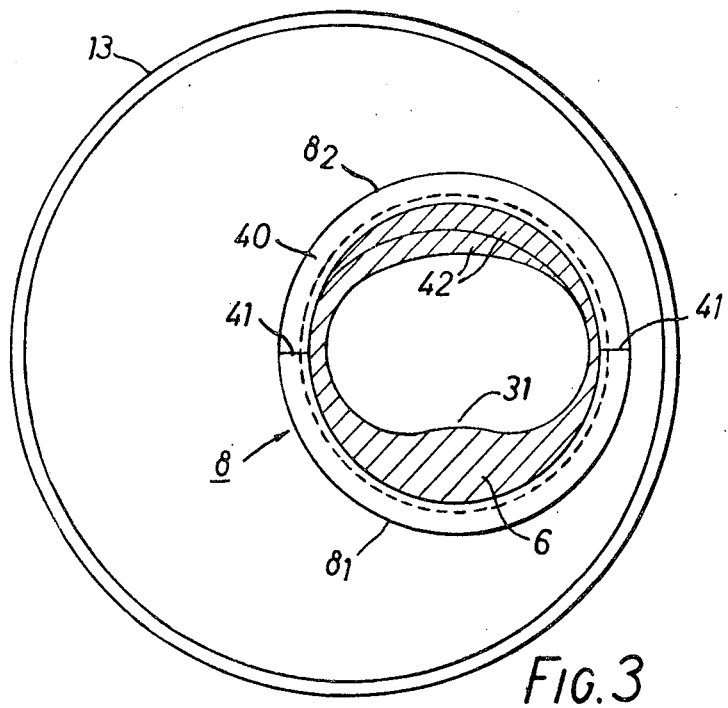
FIGS. 3 and 4 illustrates parts of the apparatus shown in FIGS. 1 and 2.
Figure 4:
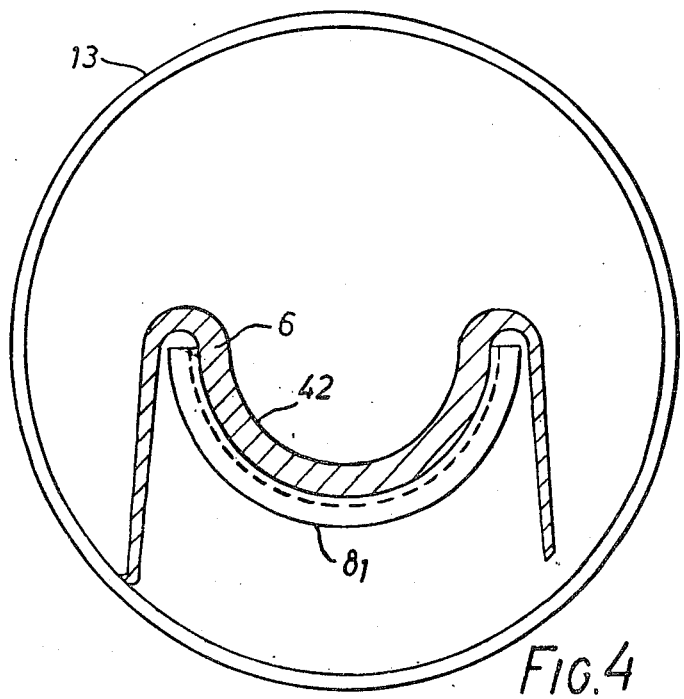
Figure 5:
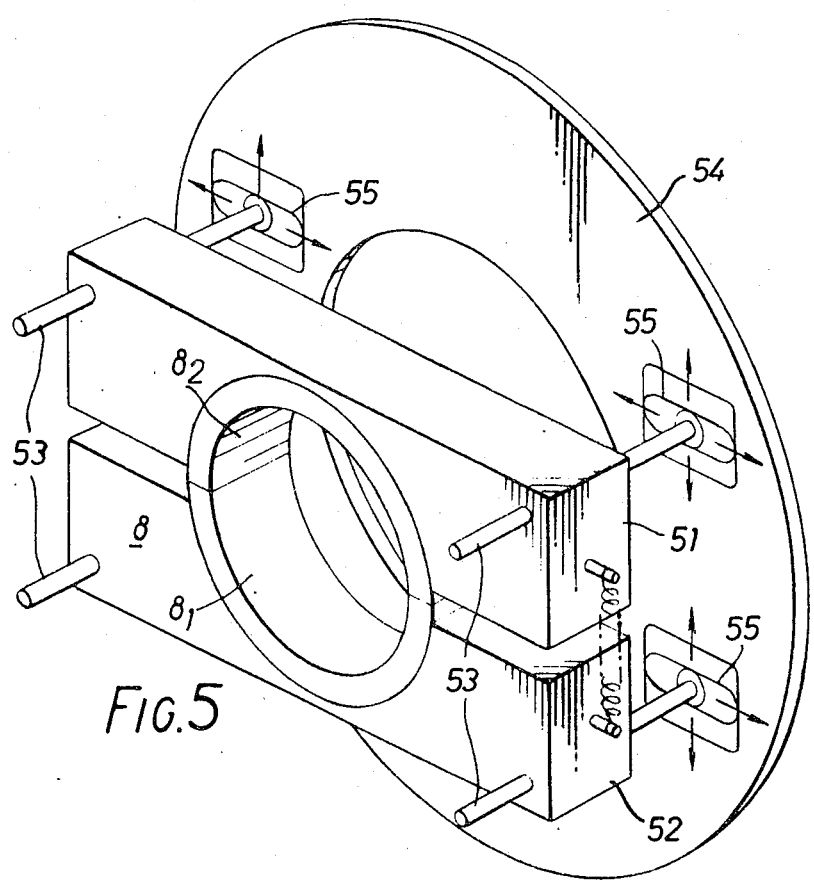
Figure 6:
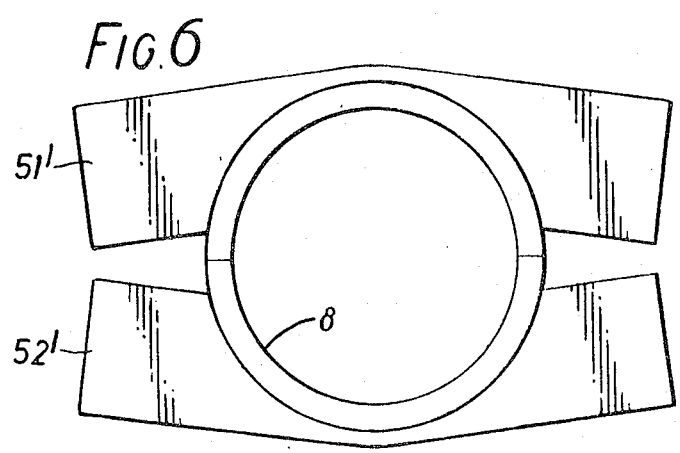

FIGS. 5 and 6 illustrate details of the attenuating mass used in the apparatus illustrated in FIGS. 1 and 2, FIGS. 7 to 10 show alternatives to FIGS. 5 and 6, and FIGS. 11 and 12 illustrate another mode of retaining the liquid medium alternative to that described in relation to FIGS. 3 and 4.

In FIG. 1 a patient 1 is shown lying on supporting means formed in two parts, 2 and 3, and his body is subject to examination by X-radiation indicated in broken line at 4. This radiation is generated by a source 5 and extends in a fan shaped or sectoral swath in a plane lying at right angles to the plane of the figure.

In the region of the exploring radiation the body of the patient is surrounded by a liquid medium, which may be water, and which has an absorption coefficient for the radiation closely similar to that of body tissue. The liquid is shown in the figure at 6 and contained within an envelope, or bag, 7. The envelope 7 is positioned within a ring like locating structure 8 which may be of metal such as duralumin. The ring structure 8 is a two part structure, as hereinafter described, and is held during operation of the apparatus in fixed relationship with other parts of the apparatus. The mounting of the ring structure 8 is such that it can be moved along the direction of the length of the patient, and moreover displaced in the plane of the exploring radiation in any direction. Thus a particular cross section of the body of the patient can be selected for examination by longitudinal traverse of the ring structure 8.

With displacement of the ring structure 8 at right angles to the axis of longitudinal traverse, the parts 2 and 3 of the patient supporting means are arranged by suitable means to suffer similar displacement, and a support 9 for the part 2 is arranged to allow of this though the means is not shown in the figure. The part 3 is supported at its end remote from the ring structure 8 by a roller 10. This roller is carried on a bearing supported by an axle member 11, which member has an axis about which rotational or orbiting motion of the X-ray source 5 takes place. The support of the part 3 by the roller 10 allows of the displacement of the part 3 along with the ring structure 8 when this is displaced laterally for the purpose of local area selection. At the other end of the part 3 to the roller 10 the part 3 is related in a hinge like manner shown at 12 to the ring structure 8, thus allowing of vertical displacement of the ring structure 8 for the purpose of local area selection.

Around the body of the patient, when he is located in position in the apparatus, there is disposed a surrounding member 13 which is cylindrical along its length having a longitudinal axis which is the axis of an angle member 11. The member 13 is closed at one end as shown in FIG. 1 and is supported at this end by a bearing 14 which, in turn, is supported by the member 11. At its other end the member 13 is open to allow of positioning of the patient within it, and at this end it is supported on rollers in the manner shown at 15. These rollers are such that the member 13 is free to rotate on its axis which, as has been indicated, is the axis about which the orbiting motion of the X-ray source 5 takes place. The source 5 is mounted on the surround member 13 by means of a support 16. Directly opposite the source 5 there is mounted on the surround member 13, by means of a support 17, a detector means 18 so as to provide radiation absorption data from which the distribution of absorption over part or the whole of the cross section of the body of the patient in the plane of the radiation from the source 5 can be determined by processing the data.

The axle member 11 is carried by the support 19 and adjacent the support 19 and surrounding the axle memer 11 is a bobbin 20. The bobbin is fixed to the support 19 and wound round it are cables 21 and 22 respectively carrying absorption data from the detector means 18 to the processing unit and supplying power for the X-ray source 5. With the orbiting motion of the source and detector means the cables wind on or off the bobbin 20. They are fed to the bobbin via respective guides 23 and 24 which are carried by the surround member 13. This member may make one-half, one or two orbiting revolutions and the cables wrap or unwrap in relation to the bobbin 20 correspondingly. At the bobbin the cables are secured and thence pass to their respective connecting units, namely the data processing unit mentioned and a power supply unit.

FIG. 2 shows an end view of the apparatus illustrated in FIG. 1 and the components identified by the reference numerals 5, 8, 13, 15, 16, 17 and 18 have the same significance as in FIG. 1. At 30 in FIG. 2 there is indicated the location of the orbiting axis and 31 shows the outline of the cross section of the patient's body in the plane of the exploring raditation. The circle 32 lying within this cross section and centered upon the orbiting axis 30 defines a selected local area, concerning which the absorption distribution is especially desired. The selection of the local area, as has been indicated earlier, is accomplished by appropriate displacement of the patient's body in a direction normal to the orbiting axis of the apparatus, and as illustrated in FIG. 2 this displacement is primarily a lateral one. The limits of the sectoral swath of radiation emanating from the radiation source 5 are denoted by the lines 35 and 36. As well be seen from the figure the detector means 18 extends over the whole spread of the fan of radiation from the source 5, namely from ray 35 at one extreme of the fan to ray 36 at the other extreme. The detector means comprises a bank of detectors for providing respective output signals indicative of the transmission or absorption of the patient's body, with respect to the radiation from the source 5, along chordal beam paths within the aperture of the patient locating structure 8.

Referring to FIG. 3 the ring structure 8 and liquid medium 6, for positioning the patient in the apparatus, is again shown in relation to the surround member 13, but in rather more detail than in FIG. 1. Thus as shown in FIG. 3 the structure 8 is flanged for purposes of rigidity at its ends as indicated in the figure at 40, and split at 41 into two halves, namely a lower half $8_1$, and an upper half $8_2$, these halves being relatively by suitable means such as pins, for example, not shown in the figure. The liquid medium 6, which as stated earlier may be water is contained within a wrap-round form of envelope, or bag, 42, corresponding to 7 in FIG. 1. This bag is located by the cylindrical portion of the ring structure 8 lying between its flanged ends. Contained within the bag the patient's body is constrained to occupy some displaced position within the surround member 13 as required by the selection of the local area for examination.

In FIG. 4 the arrangement is shown with the upper half $8_2$ of the ring structure 8 removed, and the bag 42 lying unwrapped over the lower half $8_1$ of the ring structure, this half being disposed in undisplaced relation with respect to the surround member 13. The arrangement shown is such as might be the case immediately prior to the entry of the patient into the apparatus. With entry the bag 42 is wrapped round the patient in the region of required examination, the upper half of ring 8 is fitted into place, and the bag is inflated with the liquid medium so that the medium fills the space between the patient's body and the ring. The patient and ring together are then moved along the axis of the surround member 13 until the examination region is brought under the X-ray source 5, and patient and ring are then displaced normally to the axis of 13, namely the orbital axis of the apparatus, for the required local area selection. Many ring structures such as 8, but of differing diameters, may be provided, that structure fitting most closely around the patient being chosen, so that minimum absorption of X-ray photons occurs in the liquid medium 6.

It will be realised that particularly with extreme displacements of the examined cross section in a direction away from the orbital axis of the apparatus there will be a tendency along certain rays of the fan of radiation, at least, to be subject to large variations of overall absorption in the course of the orbital motion of the apparatus. FIG. 5 illustrates means by which this effect may be obviated so that the dectector means can be operated within a limited range of excitation.

In this figure the ring structure 8 is and 8 with its two halves 81 and 82 assembled, but to avoid undue diagrammatic complexity the water bag is not shown. Fitting up against the exterior surface of the ring structure 8, however, rather in the manner of saddles are two blocks of material 51 and 52 having a coefficient of absorption, for the radiation employed, close to that of body tissue, or water. These blocks which conveniently may be made of "Perspex" fit against the ring from opposite sides. Apart from the saddle like formation enabling them to fit closely against the ring they are of essentially rectangular shape and disposed essentially parallel to one another. The blocks 51 and 52 are held against the ring structure 8 under the tension of springs, one of which is depicted in the drawing, connected between them, but this tension is not so great that the blocks cannot rotate easily around the ring 8.

Passing through the blocks 51 and 52 are four parallel rods, or slides, as shown at 53 which are arranged to lie parallel with the orbital axis of the apparatus. These rods are mounted in an annular supporting member 54, each by means of an orthogonal linear bearing as indicated at 55 in diagrammatic form. The annular supporting member 54 is fixedly related to and positioned within the surround member 13 carrying the orbiting radiation source and detector means. The slides 53 allow the ring structure 8 to be traversed parallel with the orbital axis for choosing a required plane of examination through the patient's body. The mounting of the slides permits local area selection within the examined cross section also, as may be required, but is such that the blocks lie essentially at right angles to the general direction of radiation from the source 5 at all times in the course of the orbital motion of the apparatus, the bearings 55 allowing the eccentric motion of the scanning structure with respect to the axis of the ring structure 8. During this motion the patient, in conjunction with the ring structure 8 and intervening water bag, does not move or rotate. It will be realised that with such an arrangement as has been described, and assuming the space within the ring structure 8 to be filled entirely with water in absence of the patient, then the overall absorption along the various rays of the fan of radiation from the source 5 does not change materially as the apparatus rotates orbitally. Such variation in excitation of the detector means 18 as occurs in normal operation of the apparatus is thus reduced to a minimum. It will also be realised that with the described arrangement the ring structure 8 is held be retaining means which permits its longitudinal traverse and transverse displacement for patient positioning purposes.

FIG. 6 shows a way of overcoming the possibility that the ring structure 8 may not be truly circular in cross-section but may be distorted slightly say to a form which is more strictly described as elliptical. If it is assumed that the ring 8 is distorted in this manner and that the major elliptical axis lies vertically in the plane of the paper. By making the blocks (shown as $51^1$ and $52^1$ in FIG. 6) sufficiently thin at their points of least cross-section they can be caused to be sufficiently flexible to deform under the spring tension between them and sensibly close up the air gap that would otherwise tend to exist between them and the ring structure. In this way variations of ray absorption by reason of different path lengths for different beams in the aperture of the locating structure 8 are largely reduced or eliminated.

Figure 7:
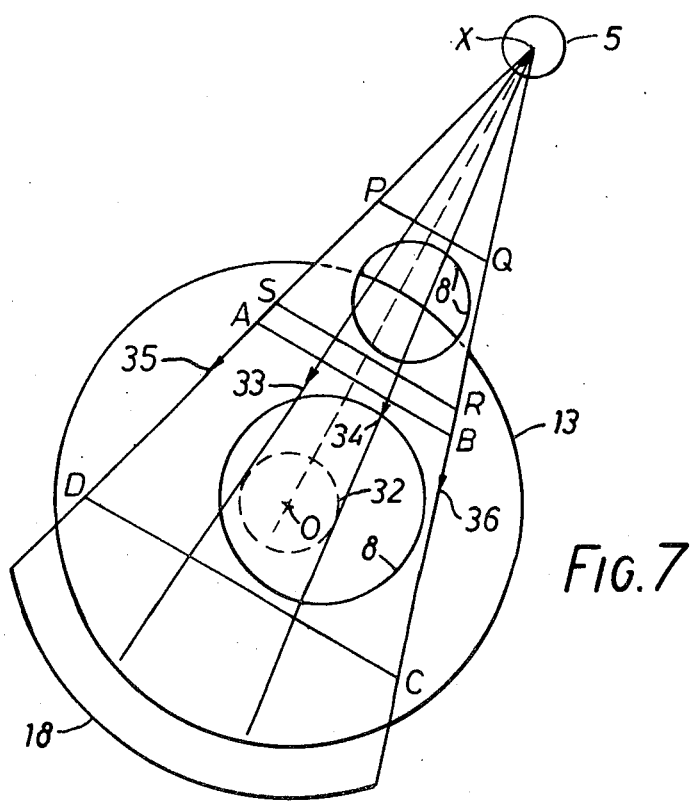

FIG. 7 is a diagram showing an alternative arrangement to that described with reference to FIGS. 5 and 6. In FIG. 7 the numeral 13 as before designates the surround member of the apparatus and 5 the X-ray source, whilst 18 indicates the detector means. The point X represents the point from which the radiation from the source 5 may be assumed to emanate. The point 0 represents the location of the orbital axis, shown at 30 in FIG. 2, this axis constituting the axis of the member 13. The point 0 is also the centre as stated earlier of the circular region selected for special examination. As shown in FIG. 7 the centre of the ring structure 8, containing the liquid medium that fills the space between the patient and the ring, is displaced wth respect to the point 0 as will generally be the case.

Numerals 33, 34, 35, 36 designate the same four rays radiating from the source 5 as are shown in FIG. 2. AB and DC are straight lines such that they represent respectively lines drawn in the uppermost surface of block 51 and in the lowermost surface of block 52 in FIG. 5, from end to end of these blocks. The line AB intersects the ray 35 in the point A and the ray 36 in the point B. Likewise the line DC intesects the ray 35 in D and ray 36 in C. For the particular location of the orbital radius OX, showing the region lying between the perimeter ABCD and the outer surface of the ring 8, represents the region of compensating absorption added in the arrangement of FIG. 5 so that, in the absence of the patient and assuming the region within the ring 8 filled with a medium of essentially the same absorption coefficient as body tissue, the overall absorption of all the rays of the radiation fan is more or less the same and does not change materially with the orbiting motion of the radius OX. This is stated assuming negligible gap between the absorbing blocks 51 and 52.

In FIG. 7 the straight lines PQ and SR also shown are like the lines AB and DC also normal to the orbital radius OX. PQ intersects ray 35 in P and ray 36 in Q, while SR intersects ray 35 in S and ray 36 in R. Moreover PQ and SR are so located that the figure PQRS is geometrically similar to the figure ABCD. In these circumstances if the region within the figures PQRS were filled with an absorbing material of the appropriate absorption coefficient for the radiation of the source 5 and if a circular aperture defined by the circle 81 were formed in the region so that the absorbing region remaining was geometrically similar to that within the perimeter ABCD, no absorption occurring within the ring 8', then the absorption of radiation passing through the apertured region PQRS would identical with that of radiation passing through the absorption compensation blocks 51 and 52, assumed just touching, of FIG. 5. By following this technique the absorption compensation material need not surround the ring structure 8 but may be disposed entirely to one side of the structure, so that absorption compensation occurs before the radiation is incident upon the patient. If the compensation associated with the perimeter PQRS is not complete it may be supplemented by additional compensation on like lines occurring within another geometrically similar absorbing region still further displaced towards the source X.

Figure 8:
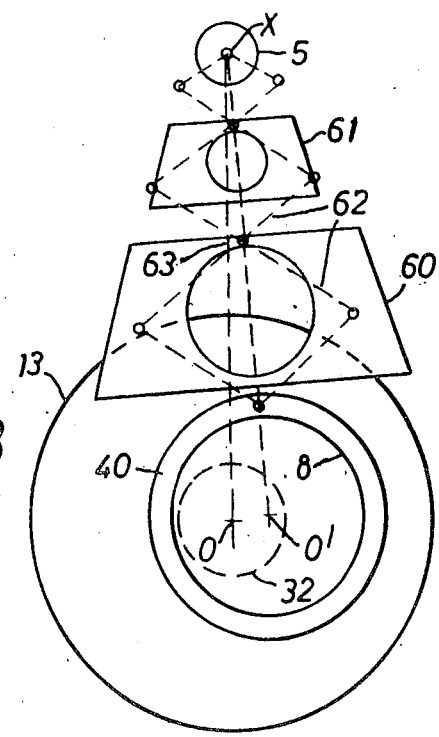

It will be realised that in general and in the course of orbital rotation the region ABCD must move both towards the source X and away from it since the axis of 0 is centric to the axis of the ring 8. Geometrical similarity of the region PQRS with region ABCD during such rotation can therefore only be maintained if region PQRS is made to undergo a like motion to that of ABCD in proportion as it is distant from X. FIG. 8 illustrates a manner of execution in practice by which this proportionate motion may be achieved.

In this figure, 13 as before, designates the surround member. 0 represents the location of the orbital axis. 5 again represents the X-ray source with X as the point from which the radiation is considered to emanate. The point 0' displaced from the orbital axis 0 represents the location of the axis of ring 8. The numeral 60 designates an apertured block of absorbing material corresponding to the apertured absorbing region associated with the perimeter PQRS in FIG. 7, though it must be understood that the block 60 extends laterally rather more than does the region PQRS in order that the whole of the swath of radiation from the source X may always pass through the block 60 no matter in what direction the orbital radius OX happens to lie in the course of the orbital motion. Apart from the matter of lateral dimensions the block 60 conforms strictly with the principles indicated in relation to the absorbing region within the perimeter PQRS in FIG. 7. Thus the uppermost and lowermost surfaces of the block 60 are maintained always at right angles to the orbital radius OX, while the centre of the aperture of the block lies on the straight line joining the point 0' with the point X, the centre of the aperture always dividing the line o'X in the same ratio.

The condition that the uppermost and lowermost surfaces of the block 60 remain normal with the orbital radius OX can be secured by means of a slide permitting the motion of the block 60 in the direction of the orbital axis OX, the association with the slide however not restricting motion of the block laterally of the orbital axis. To secure the required movement of the block in so far as the join O'X must always be divided in the same ratio by the centre of the aperture, the block is associated with a lazy-tongs mechanism 62, drawn in broken line, between the rim 40 of the ring structure 8 and an axis normal to the plane of the diagram passing through the radiation source X. The end of the lazy-tongs 62 connecting with the flange 40 is pinned to the flange at a point lying on the join O'X. The block 60 is pivoted to the cross-over point 63 in the lazy-tongs adjacent to the uppermost surface of the block. This association of the cross-over point 63 with the block may be by means of a frame (not shown) holding the block 60. FG. 8 shows a further block 61 similar to the block 60 which may be used as required to supplement the compensating action of the block 60 if this compensation is not fully complete. The block 61 is associated with the lazy-tongs 62 in a manner similar to that of the block 60.

Figure 9:
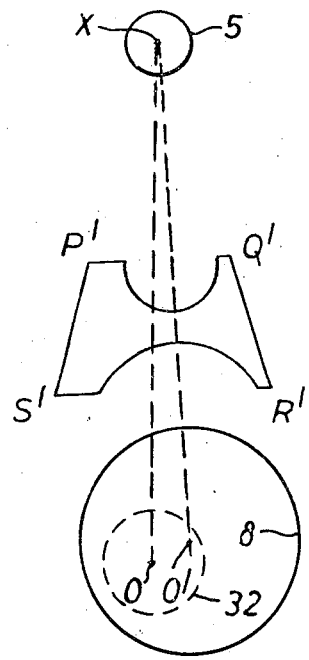

FIG. 9 illustrates a development of the arrangement that has been described in relation to FIG. 8. In FIG. 9, 0 once again represents the axis of orbital rotation and X the point from which the radiation emanates from the X-ray source 5. O' represents the location of the axis of the ring structure 8 as before. In place of the absorption compensation region bounded by the perimiter PQRS in FIG. 7, there is a compensating absorbing region represented as P'Q'R'S'. The effect of the aperture of region PQRS is provided in this configuration by the waisting that is shown in FIG. 9. The form of this waisting is such that any ray passing through the region P'Q'R'S suffers the same absorption as if it had passed through the apertured region PQRS of FIG. 7.

Figure 10:
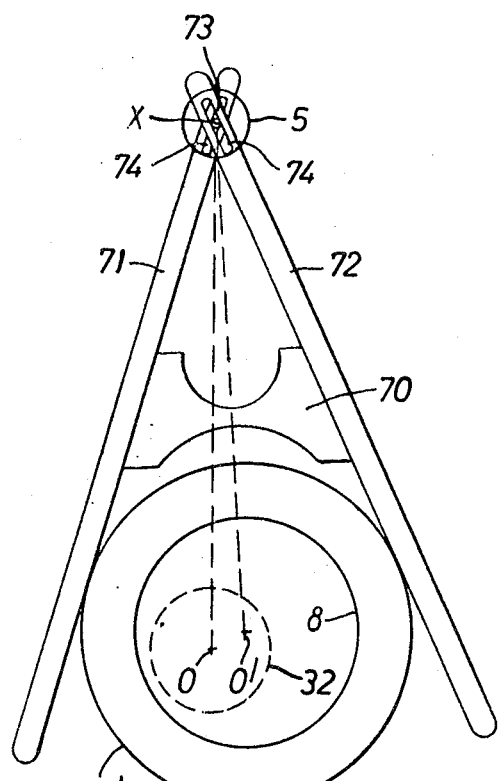

It will be realised that if a region of absorbing material on the lines of the configuration ofP'Q'R'S is to be employed in practice, then it is necessary to make provision for the movement of the region towards and away from the source X as orbital rotation takes place. This could be accomplished by means of lazy-tongs technique following the arrangement of FIG. 8 but an alternative mode of execution is indicated in FIG. 10 and is preferred. In this figure the letters O, X, O', and the numeral 8 have the same significance as in FIG. 9. The block of absorbing material 70 corresponds to the absorbing region P'Q'R'S' of FIG. 9 but is essentially symmetrical about an axis passing through the source X. For support the sides of the block 70 are bonded to respective longitudinal members 71 and 72, each of which is located at one end by a pin 73, the axis of which is normal to the plane of the paper and passes through the source X. Each of the members 71 and 72 engages with the pin by means of a slot cut in it so that each member is free to move in the direction of its length with respect to the pin 73.

Towards the other end of their length the members 71 and 72 bear on the drum surface 40' which may be considered as an extension of the rim 40 of the ring structure 8, the drum surface 40' however having a diameter rather greater than the diameter of the rim 40. The members 71 and 72 are urged towards the drum surface 40' by the tensions of springs not shown in the figure. With the arrangement so described, and with orbital rotation, the block of absorbing material 70 will move towards and away from the source 10 after the manner required. Since, however, the members 71 and 72 will need to make varying angles with one another in the course of the orbital motion, it is necessary that the block 70 should be of flexible material. The required flexing is assisted by the presence of the waist in the form of the block. The flexing of the block 70 assists moveover in the simulation with good accuracy of the absorption of rays passing through the apertured block PQRS of FIG. 7 regardless of the variations in the location of the block within the fan of radiation from the source X as orbital motion takes place.

Figure 11:
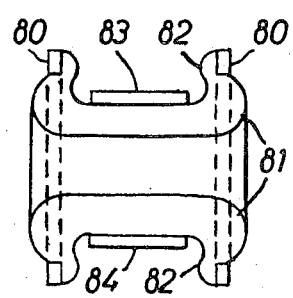
Figure 12:
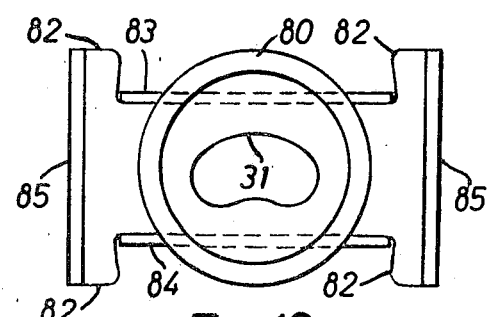

FIGS. 11 and 12 show respectively different views of an alternative to the patient locating structure 3 of FIG. 1. This alternative has the advantage of being suitable for examining patients of widely differing body dimensions. Turning to FIG. 11 the reference numberal 80 designates a pair of annular liquid seals having relatively rotatable inner and outer rings. The annular seals 80 lie parallel with one another and about an axis of rotation the same as the axis referred to earlier as located at 0', of the ring structure 8. The two rings of seals 80 are attached respectively to two parts of a water bag, namely, the part 81 and the part 82. The part 81 is attached to the inner rings of the annular seals 80 and the part 82 is attached to the outer rings thereof. The annular seals 80 allow innerand outer bay parts to rotate relative to each other. The rings of the seals 80 to which the inner part 81 of the water bag is attached, are fixed relative to the scanning structure of an apparatus in any suitable manner during a scanning operation. On the other hand the rings of seals 80 to which the outer part 82 is attached is on the other hand mounted to rotate with the scanning structure.

Assuming the patient to be in position in the apparatus, and with a portion of his body accordingly extending within the annular seals 80, inflation with water of the bag formed by the parts 81 and 82 causes the part 81 to press down on the patient's body. At the same time the part 82 becomes pressed against a pair of rigid "Perspex" cross members 83 and 84. These members lie parallel with one another and are of uniform cross-section and are mounted to move with the scanning structure.

FIG. 12 shows an end view of the arrangement as set out in FIG. 11. In FIG. 12 the numeral 31 as before designates the boundary of the cross-section of the patient's body which is under examination, and closure members 85 close off the part 82 of the water bag at its ends on each side of the patient. Assuming the patient's body to be replaced by an equal volume of water it will be seen that an attenuating mass of character essentially the same in the circumstances as that associated with the blocks 51 and 52 in FIG. 5 is provided between the upper surface of the cross-section to constitute rigid members in so far as the pressure in the water bag tends to deform them. The construction shown in FIGS. 11 and 12 can of course be adapted to other forms of apparatus according to the invention.

What we claim is:

1. Radiographic apparatus including source means for projecting radiation in a plane through a part of a body, detector means for detecting radiation emergent from said body along a plurality of beam paths in said plane, means for locating said body, relative to said source means and said detector means, with a plane of interest in said body substantially coincident with the plane of said beam paths, and scanning means for causing said source means and said detector means to rotate around said body, about an axis substantially perpendicular to said plane of interest, means being provided for adjusting the position of said body relative to said axis while maintaining the substantial coincidence of said plane of interest and the plane of said beam paths.

2. Apparatus according to claim 1 wherein the adjustment means comprise an annular supporting member secured relative to the scanning means, a plurality of rods secured relative to a component of said locating means and a plurality of orthogonal bearings each secured to the annular supporting member and cooperating with a respective one of said rods to allow for excentric rotation of the source and detector means about the axis of the location means.

3. Apparatus according to claim 2 wherein said locating means includes a ring member adapted to surround the body and the component of the locating means comprises a pair of saddle-shaped blocks adapted to rotate with the scanning means about said ring member.

4. Apparatus according to claim 3 wherein said set of bearings comprises four bearings and each of said saddle-shaped blocks is pierced by a pair of said rods, said blocks being slidable on said rods to accomodate movement of said body along the direction of said axis of rotation.

5. Apparatus according to claim 3 including resilient means for urging said blocks towards one another and into intimate contact with said ring member.

6. Medical radiographic apparatus including a source of a substantially planar spread of penetrating radiation, an apertured structure for supporting the source so as to project said radiation across said aperture, the aperture being adapted to receive a patient's body, a set of detector devices, also supporting by said support structure, positioned on the opposite side of said aperture to said source to receive radiation projected across said aperture along different paths in said plane and passing through a region of interest in the patient's body, a support for the patient's body and a ring member surrounding said body in the vicinity of said region of interest, flexible radiation attenuator means, said ring member being secured around the body so as to trap the flexible attenuator means between said ring and the body to substantially exclude air from the periphery of the body where it is surrounded by said ring member, two attenuator blocks, disposed to contact said ring member and located between the source and the body and between the body and the detector devices respectively, and supported by said support structure, for the purpose of tending to equalise the amount of radiation incident on the detector devices, despite differences in the lengths of said paths through the patient's body, means for rotating the support structure, and hence the source, the detector devices and the attenuator blocks, about an axis passing through said aperture substantially perpendicularly to the spread of radiation, with the attenuator blocks sliding around said ring member, so as to cause said source to irradiate the body from a plurality of different directions and to obtain output signals, from each said detector devices, relating to the absorption suffered by said radiation on traversing a plurality of different paths through the body in said region of interest during said rotation, orthogonal linear mountings being provided to mount said attenuator blocks to said support structure, and the apparatus thus being adapted to allow for positioning of the patient's body in said aperture with the centre of said ring member offset from the axis of rotation of said support structure.

* * * * *